(12) United States Patent
Larson et al.

(10) Patent No.: US 8,489,413 B1
(45) Date of Patent: Jul. 16, 2013

(54) SYSTEM AND METHOD FOR FACILITATING APPLICATIONS FOR DISABILITY BENEFITS

(75) Inventors: Lynn D. Larson, Las Vegas, NV (US); Dennis W. Larson, Las Vegas, NV (US)

(73) Assignee: Disability Reporting Services, Inc., Las Vegas, NV (US)

( * ) Notice: Subject to any disclaimer, the term of this patent is extended or adjusted under 35 U.S.C. 154(b) by 1158 days.

(21) Appl. No.: 12/119,142

(22) Filed: May 12, 2008

(51) Int. Cl.
*G06Q 10/00* (2006.01)

(52) U.S. Cl.
USPC ........................................ 705/2; 705/3; 705/4

(58) Field of Classification Search
USPC ............................................................. 705/2
See application file for complete search history.

(56) References Cited

U.S. PATENT DOCUMENTS

| | | | |
|---|---|---|---|
| 5,572,421 A | 11/1996 | Altman et al. | |
| 6,120,440 A | 9/2000 | Goknar | |
| 6,151,581 A | 11/2000 | Kraftson et al. | |
| 6,347,329 B1 * | 2/2002 | Evans | 709/202 |
| 6,607,482 B1 | 8/2003 | Teitelbaum | |
| 6,625,582 B2 * | 9/2003 | Richman et al. | 705/35 |
| 7,630,911 B2 * | 12/2009 | Kay | 705/3 |
| 7,630,913 B2 * | 12/2009 | Kay | 705/4 |
| 7,707,046 B2 * | 4/2010 | Kay | 705/3 |
| 2002/0138306 A1 | 9/2002 | Sabovich | |
| 2006/0074719 A1 | 4/2006 | Horner | |
| 2007/0129969 A1 | 6/2007 | Burdick et al. | |

* cited by examiner

*Primary Examiner* — Michael Fuelling
(74) *Attorney, Agent, or Firm* — Greenberg Traurig

(57) ABSTRACT

A system and method which facilitates the reliable collection of data during a single appointment through a plurality of queries configured to obtain responses or present further queries as necessary to ultimately obtain all of the information required for generating a report in a format which satisfies the applicable standards.

12 Claims, 9 Drawing Sheets

EDIT AUTHORIZING AGENCY INFORMATION

SELECT AGENCY: | WNPSC DISABILITY PROCESSING, RICHMOND, CA 94804-0109 |

GENERAL/MISCELLANEOUS AGENCY DATA

AGENCY NICKNAME: | BDA--RICHMOND |
AGENCY NAME: | WNPSC DISABILITY PROCESSING |
ADDRESS - STREET: | PO BOX 4109 |
ADDRESS - CITY, STATE ZIP: | RICHMOND, CA 94804-0109 |

SHOW/NOSHOW FAX RECIPIENTS: | SABRINA MIFUNE |
SHOW/NOSHOW FAX NUMBER: | (888) 880-2831 |

CHECK, IF TAXI ASSISTANCE IS AVAILABLE?: ☐
PHONE NUMBER FOR TAXI ASSISTANCE: | (888) 880-2830 |
CONTACT PERSON(S) FOR TAXI ASSISTANCE: | FRANCIS OR SABRINA |

CURRENT FEE SCHEDULE IN EFFECT: | 1/1/2006 -- WNPSC DISABILITY PROCESSING |

EDIT AUTHORIZING AGENCY INFORMATION

SELECT AGENCY: WNPSC DISABILITY PROCESSING, RICHMOND, CA 94804-0109

| ADJUDICATOR'S NAME | LOCAL PHONE NUMBER | EXTENSION | LD PHONE NUMBER |
|---|---|---|---|
| (NO NAME ENTERED) | | | |
| ALBERT F. NG | | 2553 | (888) 880-2830 |
| AURORA M. MATIBAG | | 1505 | (888) 880-2830 |
| BARBARA L. JOHNSON | | 1543 | (888) 880-2830 |
| BRIAN KNOX | | 1351 | (888) 880-2830 |
| CAROLYN L. TOM | | 1578 | (888) 880-2830 |
| DALE W. JOHNSON | | 2808 | (888) 880-2830 |
| DARRON K. TYLER | | 1350 | (888) 880-2830 |
| EDWARD F. FREY | | 1517 | (888) 880-2830 |
| ERIC W. WALKER | | 2473 | (888) 880-2830 |
| FLORINA DOCENA | | 1533 | (888) 880-2830 |
| GARY W. WENDLAND | | 1538 | (888) 880-2830 |
| GEORGE T. WRIGHT | | 1575 | (888) 880-2830 |
| GEORGINA ISOLA | | 2811 | (888) 880-2831 |
| GERALD X. JAN | | 1547 | (888) 880-2830 |
| JACKIE X. RICHMOND | | 1582 | (888) 880-2830 |
| JAMES X. THOMPSON | | 2813 | (888) 880-2830 |
| JIM C. BROWN | | 4646 | (888) 880-2830 |
| JOE KUHN | | 2821 | (888) 880-2830 |
| JOHN J. KUHN | | 2821 | (888) 880-2830 |
| JOHNNY SHARE | | | |
| KATHERINE A. CAVANAUGH | | 1525 | (888) 880-2830 |
| LESTER S. HORN | | 1353 | (888) 880-2830 |
| LINDA M. HOSE | | 2824 | (888) 880-2830 |
| LUCIE RODRIGUEZ | | 2582 | (888) 880-2830 |
| MICHAEL R. CUEVAS | | 1535 | (888) 880-2830 |
| NELSON D. ARCILLA | | 2473 | (888) 880-2830 |
| PAUL D. BANFORD | | 1518 | (888) 880-2830 |
| PAULA DAVIS-MCDONALD | | 1504 | (888) 880-2830 |
| SHIRLEY EVANS | | 2547 | (888) 880-2830 |
| SHSHANE M. THOMAS | | 1533 | (888) 880-2830 |
| SUSAN A. HAMPTON | | 2804 | (888) 880-2830 |
| SUSAN FOX | | 2819 | (888) 880-2830 |
| SUSAN P. GARRITY | | 1522 | (888) 880-2830 |
| VICKI J. RHOADS | | 1505 | (888) 880-2830 |

FIG. 4      106

EDIT AUTHORIZING AGENCY INFORMATION

SELECT AGENCY: BUREAU OF DISABILITY ADJUDICATION, CARSON CITY, NV 89146

|  | EDIT/ENTER | CURRENTLY ACTIVE | VARIANCE |
|---|---|---|---|
| EFFECTIVE DATE OF THESE SERVICE FEES: | 6/1/2007 | 6/1/2007 |  |
| MENTAL STATUS EXAM - ADULT: | $145.00 | $145.00 | $0.00 |
| MENTAL STATUS EXAM WITH DHQ - CHILD: | $175.00 | $175.00 | $0.00 |
| WISC-III: | $125.00 | $125.00 | $0.00 |
| WISC-IV: | $125.00 | $125.00 | $0.00 |
| WPPSI-R: | $125.00 | $125.00 | $0.00 |
| WPPSI-III: | $125.00 | $125.00 | $0.00 |
| BAYLEY SCALE OF INFANT DEVELOPEMENT: | $125.00 | $125.00 | $0.00 |
| WRAT-III: | $25.00 | $25.00 | $0.00 |
| BENDER GESTALT TEST: | $55.00 | $55.00 | $0.00 |
| VINELAND ADAPTIVE SEALE TEST: | $40.00 | $40.00 | $0.00 |
| WAIS-III: | $125.00 | $125.00 | $0.00 |
| WMS-III EXAM: | $125.00 | $125.00 | $0.00 |
| TOMM: | $38.00 | $38.00 | $0.00 |
| TRAILS A AND B: | $40.00 | $40.00 | $0.00 |
| OHA FORM: | $25.00 | $25.00 | $0.00 |
| DISCOUNT (MSE/WAIS-II/IBENDER GESTAIT): | ($40.00) | ($40.00) | $0.00 |

ADD A NEW PATIENT

| | | |
|---|---|---|
| SOCIAL SECURITY NUMBER: | 111-22-3333 | ** |
| FIRST NAME: | JOHN | |
| MIDDLE INITIAL: | Q. | |
| LAST NAME: | DOE | |
| NAME SUFFIX: | III | |
| DATE OF BIRTH: | 1/1/1980 | AGE. 27 |
| GENDER: | MALE | |
| ADDRESS LINE 1 (IF NEEDED): | | |
| ADDRESS: STREET: | 123 ANY STREET | |
| ADDRESS: CITY: | LAS VEGAS | |
| ADDRESS: STATE: | NEVADA | |
| ADDRESS: ZIP: | 44444- | |
| HOME PHONE: | (702) 555-6666 | |

ADD APPOINTMENT

**DUPLICATE SOCIAL SECURITY NUMBERS ARE NOT ALLOWED

ENTER NEW APPOINTMENT

| | |
|---:|:---|
| PATIENT: | DOE, JOHN Q. III |
| PATIENT'S AGE | ON APPOINTMENT DAY: 27 YEARS, 10 MONTHS AND 6 DAYS OLD. |
| PHYSICIAN: | L.D. LARSON, PH.D. |
| APPOINTMENT DATE: | WEDNESDAY, NOVEMBER 07, 2007 |
| APPOINTMENT TIME: | 10:00 AM    (OFFICE HOURS: 08:00 AM TO 05:00 PM) |
| AUTHORIZING AGENCY: | BUREAU OF DISABILITY ADJUDICATION, CARSON CITY, NV 89146 |
| AGENCY FEE RATES USED: | EFFECTIVE 6/1/2007 (BUREAU OF DISABILITY ADJUDICATION, CARSON CITY, |
| ADJUDICATOR: | ADNY COSPER (CARSON) |

☐ CHECK IF ANY AGENCY PROVIDED COMMENTS OR SPECIAL INSTRUCTIONS
☑ CHECK IF AGENCY PROVIDED MEDICAL RECORDS OR ATTACHMENTS

AUTHORIZED SERVICE

☑ MSE FOR ADULT (AGES 18 AND OLDER)
☐ MSE/DHQ FOR CHILD** (AGES 3 TO 18)
☐ BAYLEY SCALE OF INFANT DEVELOPMENT (AGES 1 AND OLDER)
☐ WPPSI-R** (AGES 2 TO 8)
☐ WPPSI-III** (AGES 2 TO 8)
☐ WISC-III** (AGES 5 TO 18)
☐ WISC-IV (AGES 6 TO 17)
☑ WAIS-III (AGES 16 TO 89)
☐ VINELAND ADAPTIVE (AGES 1 AND OLDER)
☐ WRAT-III (AGES 5 TO 74)
☐ WMS-III (AGES 16-89)
☐ BENDER GESTAIT (AGES 1 AND OLDER)
☐ TOMM (AGES 1 AND OLDER)
☐ OHA (AGES 1 AND OLDER)
☐ TAB (AGES 1 AND OLDER)

SPECIAL AUTHORIZATION COMMENTS: [ ]    VALUE $270.00

**NOT RECOMMENDED BECAUSE OF PATIENT'S AGE AT TIME OF APPOINTMENT

FIG. 7    112

SYSTEM AND METHOD FOR FACILITATING APPLICATIONS FOR DISABILITY BENEFITS

COPYRIGHT NOTICE

A portion of the disclosure of this patent document contains material, which is subject to copyright protection. The copyright owner has no objection to the reproduction by anyone of the patent document or the patent disclosure as it appears in the United States Patent and Trademark Office patent file or records, but otherwise reserves all copyright rights whatsoever.

BACKGROUND OF THE INVENTION

1. Field of the Invention

The present invention includes embodiments directed to systems and methods for facilitating patient data collection and the preparation of reports from collected data, and more particularly, to a system and method for automating patient data collection and preparing compliant reports for Social Security disability benefits during one appointment event.

2. Background of the Related Art

Physicians typically see large amounts of patients daily with diverse issues. In order to save time, physicians rely on information obtained through questionnaires which can be administered by a nurse or other trained worker. However, the time of a trained worker is also valuable; time spent on such tasks makes the individual unavailable to perform other specialized tasks which may be more pressing.

Thus, many of these questionnaires have been adapted to be filled in by the patient. However, this approach has its drawbacks. For example, if the patient completes the questionnaire alone, he or she may overlook or ignore some of the questions. Also, if the patient usually reads in a foreign language or has vision problems, he or she may have trouble completing the questionnaire alone.

Even if a questionnaire is fully and properly filled out, tallying of the patient's answers to determine which follow-up questions are needed is a time-consuming and tedious task. Staff or other trained workers may also inadvertently introduce errors or forget to ask for further information when the questionnaire is not properly filled out.

Therefore, patient information is often obtained from a variety of sources, including patient questionnaires, the worker's written notes and the professional's verbal or written notes taken during the examination. If the information is to be used to submit an application for benefits or governmental assistance, the transcribing of notes into the appropriate format for submission is time-consuming, tedious and often introduces the potential for errors. In many cases, there is a time limit by which reports must be submitted after a patient is seen by a professional. Ultimately, the patient may suffer from a delay in receiving benefits while the application is being completed, or because the application was not completed correctly, or not completed correctly in a timely manner.

For example, many psychologists that assess disability claimants use direct interviews to collect patient data. The dominant practice is to collect all necessary data with handwritten notes during a lengthy interview. These notes, along with any background records, are mentally organized, verbally recorded and sent to a third party for transcription. This approach ties up the psychologist during the entire data collection process and requires the doctor to process the same information, sometimes four times or more (i.e., writing the original notes, organizing these notes, speaking results into a recording device for use by a transcriber, and finally proofreading the report or application—hopefully only once). Furthermore, transcription services are expensive and delay the completion of the report while the information is being transcribed.

Therefore, there is a great need for a system and method which facilitates reliable collection of data and provides further queries as necessary to ultimately obtain all of the requisite information during one appointment to generate a report or application for benefits in a format which satisfies the applicable standards prior to the end of the appointment.

SUMMARY OF THE INVENTION

The present invention provides systems and methods which facilitate the reliable collection of data during a single appointment through a plurality of queries configured to obtain responses or present further queries as necessary to ultimately obtain all of the information required for generating a report in a format which satisfies the applicable standards.

In one embodiment, the present invention is directed to a method of generating a patient examination report in accordance with accepted standards of an applicable agency during an appointment, which includes the steps of storing a first set of data relating to the patient and the applicable agency in a patient data file; presenting a first query set relating to the patient at a first event; storing a first response data received in response to the first query set in the patient data file; analyzing the patient data file according to a preset criteria to identify further patient related data to be collected; selecting further queries to collect further patient related data based on the analysis; presenting a second query set at a second event, wherein the second query set includes the selected further queries; storing a second response data received in response to the second query set in the patient data file; and generating the patient examination report in accordance with the accepted standards of the applicable agency, wherein the examination report is capable of being completed during the second event.

The preset criteria is selected so that if the patient data file satisfies the preset criteria, it contains sufficient data to generate a patient examination report complying with the accepted standards required by the applicable agency. Thus, the preset criteria may be used to identify possible errors, data inconsistencies, and missing information in the patient data file. The preset criteria may also identify subject areas for further investigation based on the accepted standards of the applicable agency. The further investigation may be conducted by a physician or other trained professional.

The further queries may therefore be selected to clarify possible errors, data inconsistencies, and missing information in the patient data file based on the accepted standards of the applicable agency. The further queries may also be intended to further investigate subject areas identified by the analysis.

In one embodiment, the applicable agency is the U.S. Social Security Administration. In one embodiment, the first event and second event occur during a single appointment, which may occur at one location, such as a specialized facility.

The data collected is generally of the type necessary to determine the patient's relative ability to work. In one embodiment, the first query set collects information relating to the medical background and social history of the patient. The second query set may also collect health related information or include requests for specialized testing. Thus, the second response data may include the results of specialized tests conducted during the second event.

In one embodiment, the present invention is configured for inserting data contained in the patient data file into a series of preset strings of words to form sentences in the examination report. The invention may be configured for adjusting a first portion of a preset strings of words to form a grammatically correct sentence in the examination report based on the data contained in the patient data file, and inserting data contained in the patient data file into a second portion of the preset string of words to form a complete sentence in the examination report.

The present invention may also be configured for analyzing the patient data file according to the preset criteria after storing the second response data, identifying any insufficient patient related data, presenting the identified insufficient patient related data in an interface, and receiving an instruction to generate the report with the insufficient data, remove the insufficient patient related data from the examination report, or allow the insufficient patient related data to be edited. Alternatively, the invention can be configured for inserting the data into a series of preset strings of words to form sentences in the examination report, analyzing the examination report to identify sentences containing insufficient data, and presenting the identified sentences in an interface, wherein the interface is configured to receive an instruction to generate the examination report with the identified sentence, allow editing of the identified sentence, or remove the identified sentence from the examination report.

The present invention is also directed to a system for generating a patient examination report in accordance with accepted standards of an applicable agency during an appointment. The system may include a database for storing a first set of data relating to the patient and the applicable agency in a patient data file; an interface for presenting a first query set relating to the patient at a first event; a database for storing a first response data received in response to the first query set in the patient data file; a data processor for, among other things, analyzing the patient data file according to a preset criteria to identify further patient related data to be collected and selecting further queries to collect further patient related data based on the analysis; an interface for presenting a second query set at a second event, wherein the second query set includes the selected further queries; and a database for storing a second response data received in response to the second query set in the patient data file.

In this embodiment, the data processor is also configured to generate the patient examination report in accordance with the accepted standards of the applicable agency prior to the end of the second event. It should also be noted that the interfaces may be the same or different.

The present invention is also directed to a machine readable media for generating a patient examination report in accordance with accepted standards of an applicable agency during an appointment. The media of the present invention may include a plurality of data segments and code segments.

In one embodiment, the media of the present invention includes data segments for storing a first set of data relating to the patient and the applicable agency in a patient data file; storing a first response data received in response to the first query set in the patient data file; and storing a second response data received in response to the second query set in the patient data file. This media also includes code segments for presenting a first query set relating to the patient at a first event; analyzing the patient data file according to a preset criteria to identify further patient related data to be collected, selecting further queries to collect further patient related data based on the analysis; presenting a second query set at a second event, wherein the second query set includes the selected further queries; and generating the patient examination report in accordance with the accepted standards of the applicable agency, wherein the examination report is completed prior to the end of the second event.

These and other aspects of the system and method of the subject invention will become more readily apparent to those having ordinary skill in the art from the following detailed description of the invention taken in conjunction with the drawings.

BRIEF DESCRIPTION OF THE DRAWINGS

So that those having ordinary skill in the art to which the present invention pertains will more readily understand how to make and use the method and system of the present disclosure, embodiments thereof will be described in detail herein below with reference to the drawings, wherein:

FIG. 3 is an exemplary user interface screen for entering information relating to the applicable agency for receiving benefits applications in accordance with the embodiments of the present invention;

FIG. 4 is an exemplary user interface screen for entering adjudicator information relating to the determination of disability benefits in accordance with the embodiments of the present invention;

FIG. 5 is an exemplary user interface screen for entering a fee structure for authorized services provided to patients on behalf of the agency in accordance with the embodiments of the present invention;

FIG. 6 is an exemplary user interface screen for entering patient information in accordance with a preferred embodiment of the present invention;

FIG. 7 is an exemplary user interface screen for entering appointment information in accordance with a preferred embodiment of the present invention;

DETAILED DESCRIPTION

The present invention is directed to systems and methods for facilitating individual reports, claims or applications for benefits to a government or administrative agency authorized to receive and adjudicate on such claims, by obtaining the necessary individual data, including any background, medical or testing data, and presenting the data in the appropriate format required by the relevant agency.

Although features and elements of the present invention is discussed herein as being applied to systems and methods for providing compliant reports to the government agency authorized to dispense Social Security benefits, it should be readily apparent that this is only one use of the present invention, and further that the systems and methods of the present invention may be employed for other uses as well.

In one embodiment, a system and method of the present invention comprises a platform, such as a conventional computing system, which includes multiple terminals, a program for querying and collecting patient data through a patient terminal, a data processor for analyzing the patient data and comparing the patient data with the data necessary for providing a comprehensive consultative examination (CE) report complying with accepted standards set forth by the Social Security Administration for submission to a state Disability Determination Service (DDS) office, to determine whether collecting further patient data is necessary, notifying the medical professional of the need to collect further patient data through a user terminal, receiving and entering the further patient data as a compliant report is generated.

Figure 8:
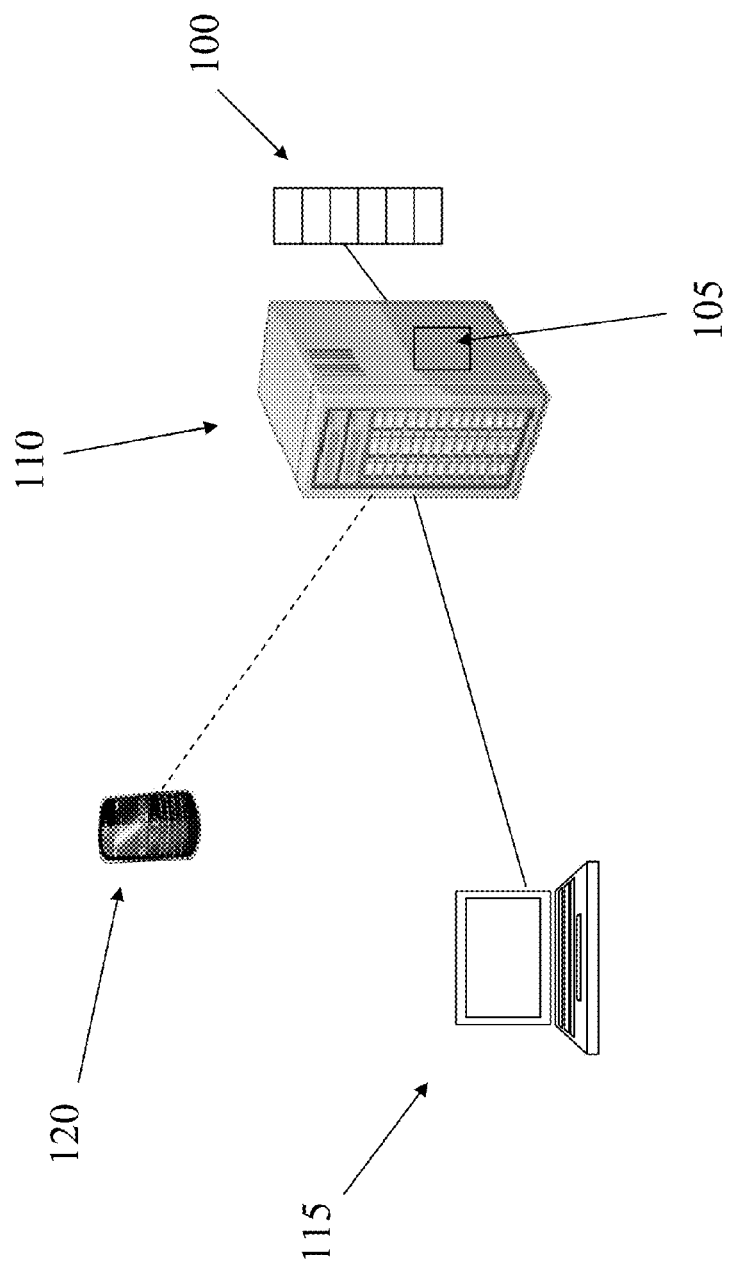
FIG. 8 is an exemplary system according to the embodiments of the present invention.

Those skilled in the art will readily appreciate that a system in accordance with the present invention may include various computer and network related software and hardware. For example, a system for implementing the method of the embodiments of the present invention, as shown in FIG. 8, may use programs, operating systems, memory 100, data storage devices, input/output devices, distributed computing networks, data processors 105, servers 110 with links to data communication systems, wireless or otherwise, such as those which take the form of a local or wide area network, and a plurality of data transceiving terminals within the network, such as personal computers 115 or hand-held devices 120. Those skilled in the art will further appreciate that, so long as its users are provided with access to the system and method of the invention, the precise software and hardware used is not vital to its full implementation.

One embodiment of the invention includes graphical user interfaces (also referred to herein as "interface screens" or "screens") having generally user-friendly features and which correspond with the overall appearance of conventional operating system interfaces screens. For example, the screens may be in a framed form, with toolbars, drop-down menus, embedded links to other screens, etc. The screens can include various other selectable features that are accessed through actuation of animated graphical representations of depressible buttons or checkboxes, which may be selected (i.e., "clicked on") by the user via a connected mouse, keyboard, voice command, touchpad, touchscreen, pointer or any other tool used for indicating a preference in a computerized graphical interface.

Figure 1:
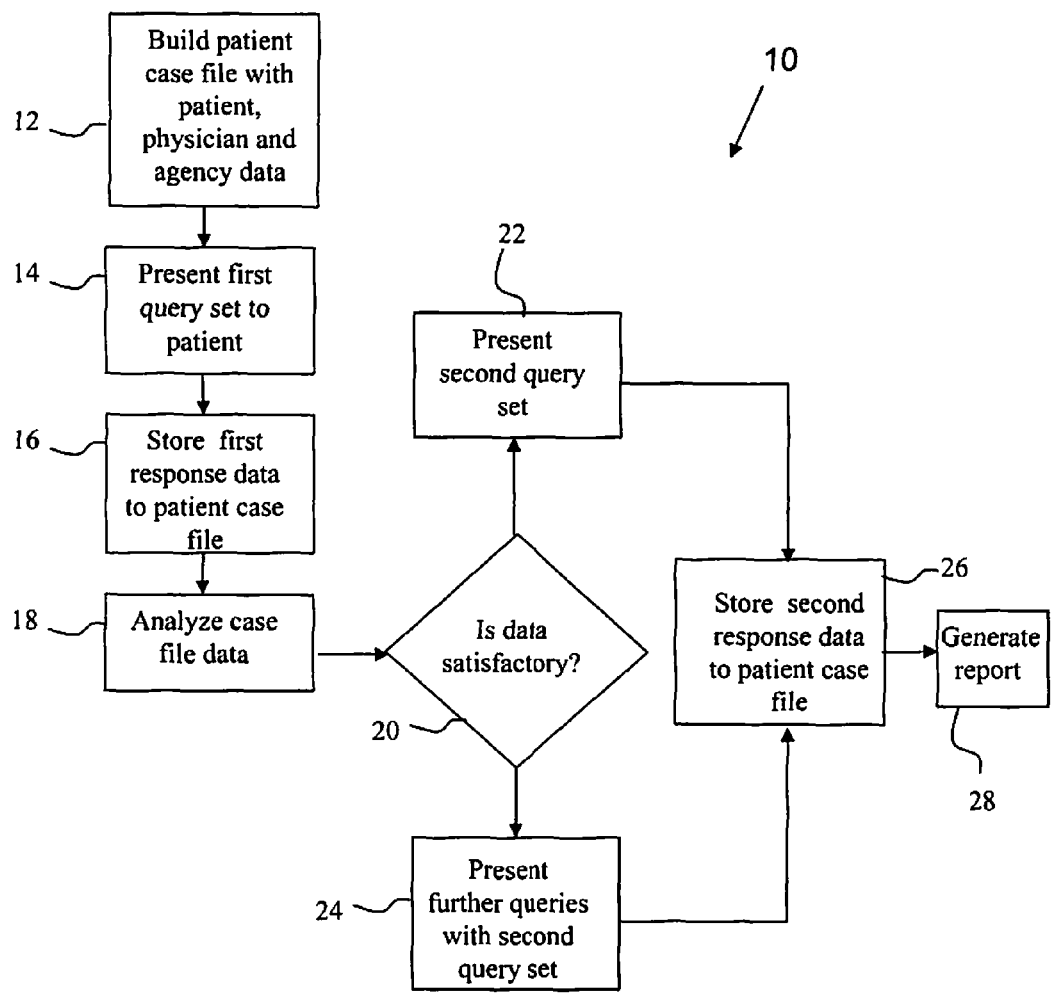
FIG. 1 is a flow chart illustrating the method of an embodiment of the present invention.

FIG. 1 illustrates a high level flow chart of a preferred embodiment of the system and method of the present invention referred to generally by the numeral 10. In step 12, a case information file is formed containing the patient, physician (or medical professional) and the relevant agency information, which may be stored as a data file in an onsite or offsite database operatively associated with system 10.

In one embodiment, step 12 is carried out prior to the appointment, and as discussed further herein, may be part of a case information intake portion of system 10 and trigger appointment notifications to the patient and medical professional, among other things.

As shown in step 14, system 10 presents a first query set relating to the patient. In one embodiment, this occurs at the appointment itself and may be carried out by the patient or individuals accompanying the patient through an onsite interface, such as via a computer terminal in a waiting area. However, since this first query set is primarily intended to be completed without assistance from a staff member, system 10 may also provide for an offsite interface, such as a website which may be accessed using a home computer with link to the world wide web.

In step 16, system 10 stores the response data to the first query set to the patient case file created in step 12. In step 18, system 10 analyzes the data to determine whether there is a need for further queries or follow-up information based at least partially on the sufficiency of the responses to the first query set in comparison to the criteria which must be satisfied in order to provide a report that meets accepted agency standards. This may be conducted by a program and processor operatively associated with system 10, and is discussed in further detail herein.

In decision step 20, if the data meets the criteria, a second query set is presented in step 22. If the data does not meet the criteria, further queries are presented along with the second query set in step 24.

It is envisioned that response data to the second query set in steps 22 or 24 (i.e., with or without the further queries) is likely to be provided by a physician using a second interface during the appointment in a private examination room during the examination. As discussed further, the second query set is designed to follow the examination report guidelines.

In one embodiment, the second query set, with or without the further queries, is presented in steps 22 or 24 either as incomplete sentences that can be finished by indicating the missing portions of the sentence which are appropriate to the particular situation, thus resulting in a completed sentence to be added to the report, or questions which upon entering a response will cause an appropriate statement to be inserted in the completed report.

In step 26 the response data to the second query set, with or without the responses to the further queries, is stored as second response data. Since the queries and data collected was at all times intended to satisfy the criteria necessary to generate a report according to the accepted standards, the response data should be sufficient to generate a report as shown in step 28.

Figure 1A:
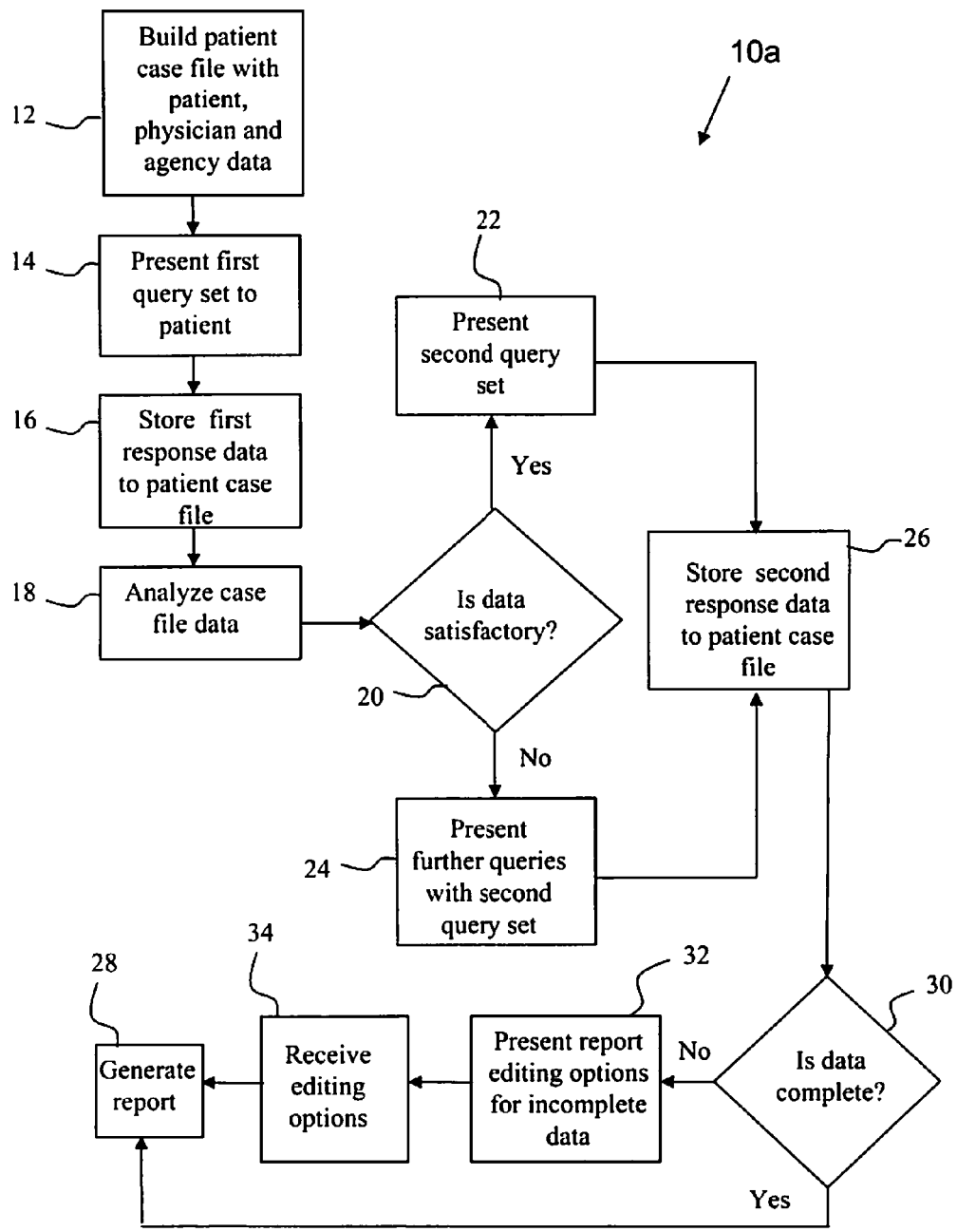
FIG. 1A is a flow chart illustrating the method of another embodiment of the present invention.

Alternatively, as shown in FIG. 1A, a system 10a may include the steps shown above with regard to system 10 and an additional analysis described further herein. The second response data is stored in step 26. In step 30, the data is checked for completion, that is, whether or not all desired data for the report has been obtained. If so, the final report is generated in step 28. If report data is incomplete or unsatisfactory, report editing options are presented in step 32. The presentation may be made via an interface in which the missing or incomplete data identified in step 30 is highlighted for convenience sake. The report editing options provided in step 32 may include providing a system user with the opportunity to view, edit or delete the incomplete data and/or the corresponding portion of the report. The user selected editing options are received in step 34 and a final report is generated based on the user input.

FIGS. 2-7 illustrate a case information intake portion of system 10 in accordance with a preferred embodiment of the present invention. The intake portion generally corresponds to step 12 shown in FIG. 1, and in this embodiment involves receiving and storing initial data regarding patients, medical professionals and the relevant government agencies, in a database. In the preferred embodiment, a case file will be created for each individual patient desirous of obtaining disability benefits through the Social Security Administration.

System 10 can provide a user terminal or interface with various screens to facilitate capturing all of the pertinent data. In one embodiment, a single entry of data will be carried over to other screens, and the inputted data can be used by system 10 to create physical files, labels, letters, emails, automated phone messages or other internal or external communications thereafter.

Figure 2:
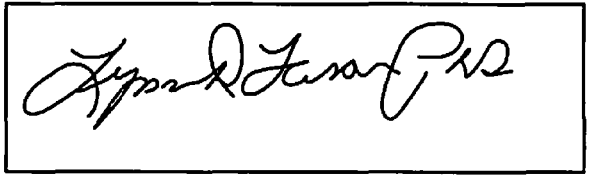
FIG. 2 is an exemplary user interface screen for entering user and/or physician information in accordance with the embodiments of the present invention.

Referring now to FIG. 2, a screen 102 includes various fields for providing information relevant to a medical professional or physician involved in the collection of data. In the current example, the physician's name, address, licensing and contact information may be entered into system 10. An electronic signature and checkboxes which may be used to indicate ownership of various medical kits are also included.

FIGS. 3-5 illustrate screens 104, 106 and 108, respectively, which allow entry of address or contact information about the relevant government agency which receives, authorizes patient appointments and/or adjudicates patient applications for benefits. In the current example, the agency listed is a application processing center. The adjudicators are shown in screen 16 and applicable fee structure, as set forth by the Disability Determination Services in the current example, is included in screen 108.

FIG. 6 illustrates a screen 110 for entering patient details, such as name, address, date of birth, etc., as required to establish a patient case file in a database operatively associated with system 10. FIG. 7 illustrates a screen 112 in which appointment information may be entered relevant to the patient entered in screen 110 and stored in the patient case file. The authorizing agency information and corresponding services authorized can also be entered in screen 112. System 10 automatically calculates the anticipated expenses depending on the services checked in screen 112. The patient information will be stored in the patient's individual case file.

System 10 may be configured to determine the next suitable appointment for the patient based on the current patient information, scheduling needs, travel requirements, holiday or vacation schedules, physician information, or other constraints known to system 10.

Prior to a scheduled appointment, system 10 may communicate with the patient, such as by transmitting e-mails, automated phone messages, by printing of appointment notification and reminder letters, or in any other way intended to encourage patient attendance and provide them with contact and office location information. System 10 may also communicate to other entities or services as necessary to facilitate transportation for the patient, or provide detailed traveling instructions or directions for using public transportation between the patient's home and the location of the appointment. System 10 may further communicate with a staff member or designated call center to provide all upcoming appointments with associated patient names and contact information to facilitate appointment notification and reminders to be sent from a third party.

System 10 is configured to communicate with the physician involved with the appointment to provide the physician with relevant details, such as by email or printing an appointment schedule for the physician. The physician can also be notified and reminded in the same manner described above for patients.

System 10 is further configured to include a patient information intake portion in combination with a preferred embodiment of the present invention. Although a professional staff member may conduct or participate in submitting information in this portion, it is envisioned that patient-related data will likely be entered by the patients themselves, or someone accompanying the patient, such as a parent, spouse, child or friend, for example, without staff assistance. Thus, in the preferred embodiment, the patient information intake portion is also referred to as the "patient interview."

To facilitate data entry, system 10 includes a patient terminal interface and is configured to communicate with patients without the need for employee or physician intervention. System 10 is set up to allow patients to enter information in direct response to preset questions or otherwise in accordance with guided instructions provided by system 10. In one embodiment, the terminal interface is any conventional device configured for transceiving data, such as for example, a personal computer with a mouse and keyboard, an audio system with voice-recognition capability, or the like.

In one embodiment, system 10 employs user-friendly screens and formats permitting patients to select appropriate information as responses to queries in a timely manner with minimal difficulty. For example, where possible, system 10 provides the option to respond to queries by using checkboxes, drop-down menus, fields or the like that include lists of possible responses for selection by the patient. Paper forms may also be substituted in the case of system downtime or depending on patient needs. Screens and queries used by system 10 may also be provided in languages other than English upon request.

In one embodiment, the patient interview queries are intended to collect as much information about the patient as can be collected for generating a CE without input from a medical professional. This may include demographic and background information, and is also intended to locate subject areas that require further investigation by the medical professional. The response may thus initiate a need for further dialog either by system 10 providing additional queries or by notifying a physician or user of the need to query the patient further about a particular subject. Any information collected using the patient terminal interface is stored in the patient case file.

Typical queries regarding the patient using the patient terminal interface are illustrated below. For convenience sake, one data entry field per query is shown (in [brackets]) in the below example. However, it should be readily apparent that additional data entry fields would be available to allow the patient (or someone on the patient's behalf) to enter as much information and details as possible. Furthermore, some of these questions may be asked by a professional during another portion of the appointment. System 10 may also provide hyperlinks to assist patients in navigating quickly through the screens. It should be readily apparent that the invention may incorporate any interface, schemes or methods for selecting one or more answers as needed depending on the information sought, such as for example, checkboxes, selectable indicia, voice-recognition, touch-sensitive screens, conventional drop-down menus with highlighted options, or combinations thereof.

General Information (Adult and Children)

1. MEDICAL HISTORY: List major illnesses and injuries. Provide approximate date of each illness or injury, your age at the time and treatment received. Start with the most recent and work back in time. Do not forget serious childhood illnesses, injuries or surgeries. Indicate if hospitalization, psychiatric treatment or treatment for drug or alcohol abuse was required.
   ☐ Check here if this does not apply because you have never had major illness or injury.
[YEAR] [HEALTH PROBLEM AND TREATMENT RECEIVED]

2. CURRENT PRESCRIPTION MEDICATIONS: List all prescription medications you are currently taking, reason for medication and doctor prescribing the medication.
   ☐ Check this box if this does not apply because you are not taking prescription medications.
[MEDICATION] [REASON FOR MEDICATION/PRESCRIBED]

3. MARITAL HISTORY: Give approximate dates of any marriages and divorces and indicate whether any marriage has been terminated by death of spouse. Also, indicate spouse's occupation and the names and ages of children born from the relationship.

☐ Check this box if this does not apply because you have no marital history.

[YEAR] [MARITAL CHANGE] [RELATIONSHIP INFORMATION]

4. WORK HISTORY: Describe your work history, starting with most recent and work back in time:

☐ Check this box if this does not apply because you have no work history.

[FROM YEAR] [TO YEAR] [WORK INFORMATION]

MEDICAL AND SOCIAL HISTORY—ADULT EDITION

All items are to be answered by placing a check mark in the box next to the correct answer or answers as indicated by the question OR by filling in the blanks.

| This form is being filled out by: | | | |
|---|---|---|---|
| ☐ Myself | ☐ Foster mother | ☐ Sister | ☐ Other Relative |
| ☐ Wife | ☐ Foster father | ☐ Brother | ☐ Case Worker |
| ☐ Husband | ☐ Stepmother | ☐ Grandmother | ☐ Female Friend |
| ☐ Mother | ☐ Stepfather | ☐ Grandfather | ☐ Male Friend |
| ☐ Father | ☐ Aunt | ☐ Uncle | ☐ Other |

Name of person filling out this form:
[FIELD]

How did the patient arrive for the appointment?
(The user would be able to select one answer from drop down menu providing the following exemplary answers: drove self, driven by another, walked, and took public transportation.)

Who did the patient arrive with for the appointment?
(The user would be able to select one answer from drop down menu providing the following exemplary answers: self, wife, husband, mother, father, and friend. If "self" is selected, system 10 may skip over any other questions relating to who arrived for the appointment with the patient. If "friend" is selected, system 10 may then provide a field for data entry so that the name and gender of the friend may be entered.)

Did the patient arrive with anyone else for the appointment?
(The user would be able to select one answer from drop down menu providing the following exemplary answers: wife, husband, mother, father, friend and nobody else. Again, if "friend" is selected, system 10 may then provide a field for data entry so that the name and gender of the friend may be entered. If "no" is selected, system 10 would not ask this question again.)

Do you know your birth father?
(The user would be able to select one answer from drop down menu consisting of "Yes" and "No" answers. If "No" is selected, system 10 automatically skips the next questions concerning the birth father.)

Your birth father's FIRST name: [FIELD]
Your birth father's LAST name: [FIELD]
Your birth father's primary occupation: [FIELD]

Is your birth father deceased?
(The user would be able to select one answer from drop down menu consisting of "Yes," "No" and "Don't Know" answers.)

Do you know your birth mother?
(The user would be able to select one answer from drop down menu consisting of "Yes" and "No" answers. If "No" is selected, system 10 would automatically skip over any of the following questions concerning the birth mother.)

Your birth mother's FIRST name: [FIELD]
Your birth mother's LAST name: [FIELD]
Your birth mother's primary occupation: [FIELD]

Is your birth mother deceased?
(The user would be able to select one answer from drop down menu consisting of "Yes," "No" and "Don't Know" answers.)

Your DATE of birth: [FIELD]
Your PLACE of birth: [FIELD]
Your Social Security number: [FIELD]
How many brothers do you have? [FIELD]
How many sisters do you have? [FIELD]
How many brothers and sisters were older than you? [FIELD]

Did you move frequently while growing up? (Check One)
(The user would be able to select one answer from drop down menu consisting of "Yes," "No" and "Don't Know" answers.)

What was the highest grade completed while in school? (Check One) (The user would be able to select one answer from drop down menu providing the following exemplary answers: Elementary School First Grade, Elementary School Second Grade, Elementary School Third Grade, Elementary School Fourth Grade, Elementary School Fifth Grade, Elementary School Sixth Grade, Jr. High (Seventh Grade), Jr. High (Eighth Grade), Jr. High (Freshman), High School (Sophomore), High School (Junior), High School (Senior), and Beyond High School.)

What kind of classes did you attend while in school?
(The user would be able to select one answer from drop down menu providing the following exemplary answers: All regular classes, Regular classes with some Special ed. classes, Special ed. classes with some Regular classes, and All Special ed. classes)

What best describes the result of you high school education?
(The user would be able to select one answer from drop down menu providing the following exemplary answers: Regular diploma from high school, Certificate of attendance from high school, GED after leaving school, Have not completed high school.)

How did you do as a student while in school?
(The user would be able to select one answer from drop down menu providing the following exemplary answers: Very Poor, Poor, Below Average, Average, Above Average, and Excellent.)

List extra activities you participated in while in school: (Such as clubs, athletics, music, leadership, or social activities): [FIELD]

What education have you attained beyond high school?
(The user would be able to select one answer from drop down menu providing the following exemplary answers: None, Completed some Technical/Trade courses, Received a Technical/Trade Certificate, Completed some college courses, Received an Associates Degree, Received an Professional Diploma, Received a Bachelors Degree, Received a Masters Degree, and Received a Doctorate Degree.)

What has been your primary occupation? [FIELD]
How many years did you work in your primary occupation?
(The user would be able to select one answer from drop down menu providing the following exemplary answers: Does Not Apply, Less than 1 year, 1 year, 2 years, 3 years, 4 years, 5 years, 6 years, 7 years, 8 years, 9 years, 10 years, and More than 10 years.)

What other occupations have you had? [FIELD]
How many years did you work in other occupations?
(The user would be able to select one answer from drop down menu providing the following exemplary answers: Does Not Apply, Less than 1 year, 1 year, 2 years, 3 years, 4 years, 5 years, 6 years, 7 years, 8 years, 9 years, 10 years, and More than 10 years.)

Have you served in the Armed Forces?

(The user would be able to select one answer from drop down menu consisting of "Yes" and "No" answers. If "No" is selected, system 10 would skip over any of the following questions regarding serving in the Armed Forces.)

If "Yes", what branch of service?
(The user would be able to select one answer from drop down menu providing the following exemplary answers: Air Force, Army, Coast Guard, Marine Corp, National Guard and Navy)

If "Yes", how many years served?[FIELD]
If "Yes", highest rank attained? [FIELD]
If "Yes", type of discharge? (Check One)
☐ Medical Discharge
☐ Honorable Discharge
☐ Dishonorable Discharge How long have you lived in the Southern Nevada area?
(The user would be able to select one answer from drop down menu providing the following exemplary answers: Does Not Apply, Less than 1 year, 1 year, 2 years, 3 years, 4 years, 5 years, 6 years, 7 years, 8 years, 9 years, 10 years, More than 10 years and All my life. It should be noted that this question is dynamic in that the geographic area used in the question will change depending on the location of the physician as entered in system 10.)

Dwelling type? (Check One)
☐ Rented apartment
☐ Rented home
☐ Owned home
☐ Mobile home
☐ Room in a home
☐ Group home
☐ Other With whom do you now live? (Check One)
(The user would be able to select one answer from drop down menu providing the following exemplary answers: Alone, Spouse only, Spouse and children, Children, Parents, Roommate of same sex, Roommate of opposite sex, Relatives, Friends, Ex-spouse, and Other.)

Do you receive: (Check All That Apply)
☐ ADC
☐ Welfare
☐ Regular Social Security
  ☐ SSI
  ☐ Social Security Disability
☐ Medicaid
☐ Medicare
☐ Food Stamps
☐ Alimony
☐ Child Support
☐ Other [FIELD]
☐ No support received Are you experiencing physical pain at this time? (Check One)
(The user would be able to select one answer from drop down menu consisting of "Yes" and "No" answers. If the user selects "Yes," system 10 provides further questions regarding physical pain, whereas these questions are skipped over by system 10 if the user selects "No.")

For example, if "Yes", is selected, a question such as the following may be provided:

What part of your body typically hurts the most?
(The user would be able to select one answer from drop down menu providing the following exemplary answers: Head, Neck, Upper limbs, Lower limbs, Back, Stomach, Several body areas, Entire body, and None of the areas listed.)

How long have you been having this pain?
(The user would be able to select one answer from drop down menu providing the following exemplary answers: Within the past six months, Six months to one year, One to two years, Two to four years, and Over four years.)

How severe has the pain been recently? (Check One)
(The user would be able to select one answer from drop down menu providing the following exemplary answers: Mild, Discomforting, Distressing, Horrible, and Beyond description.)

How often does this pain occur? (Check One)
(The user would be able to select one answer from drop down menu providing the following exemplary answers: Monthly, Weekly, Daily, and All the time)

How often do you take prescribed medications for this pain? (Check One)
(The user would be able to select one answer from drop down menu providing the following exemplary answers: Never, Seldom, Occasionally, Often, Frequently, and All the time)

Do you use any of the following to reduce the pain? (Check All That Apply)
☐ Heat/Cold treatment
☐ Electrical stimulation or TENS unit
☐ Physical Therapy or Exercises
☐ Lie Down
V None of the above Do you have a history of seizures or convulsions? (Check One)
(The user would be able to select one answer from drop down menu consisting of "Yes" and "No" answers. If the user selects "Yes," system 10 provides further questions regarding seizures or convulsions, whereas these questions are skipped over by system 10 if the user selects "No.")

What type of seizures have you experienced? (Check One)
(The user would be able to select one answer from drop down menu providing the following exemplary answers: Grand Mal, Partial, Jacksonian, Petit/Mal/Absence, Myoclonic, and Other.)

As can be seen from the above, system 10 may be used to solicit a variety of data, and provide further "follow-up" queries based on the responses to obtain additional information.

It should be readily apparent that more or other queries, in the form of questions or requests for information or the like, may be posed in accordance with the preferred embodiment. It should be readily apparent that many questions covering many subjects may be provided, and significant amounts of data may be collected, in accordance with the present invention. In one embodiment, the questions are primarily intended to collect the information which is necessary for generating the reports used to obtain disability benefits.

Once the patient interview portion is complete, a user, staff member, trained professional or other user using an additional interface in communication with system 10 accesses the patient interview and may clarify or add information relating to the patient by themselves or request further information from the patient. In one embodiment, system 10 provides a series of queries for the user to follow based on the responses to the queries provided during the patient interview portion or per regulations or standards set forth by the authorizing agency.

For example, system 10 may prompt a staff member to input observational information relating to the arrival and appearance of the patient at the time of the appointment, such as the time the patient showed up for the appointment and the manner of transportation used to arrive at the office. In one embodiment, system 10 is configured to recognize each response given during the self-interview and indicate problems or issues with regard to the patient to the staff or medical professional for further investigation.

The appointment with the physician (e.g., a medical doctor, psychologist, social worker or other professional trained to examine the patient) may involve specialized tests or examinations, as well as further inquiry, all of which may be carried out with the physician entering the data into an interface in communication with system 10. Thus, the physician's findings will be stored to the case file connected with the particular patient. The physician, an assistant or trained professional (i.e., user) is also provided with a user-friendly query or data entry system during the appointment which is similar to the one shown above for use with the patient interview.

The queries, which may also be posed as partial statements to be completed with appropriate information, may themselves be selected pursuant to the data entered by the patient during the self-interview portion and finalized during the appointment. Some information may be missing or inconsistent and require follow-up and clarification, whereas other information must receive input from a physician to be acceptable to the authorizing agency.

The queries are intended to provide a final report which is acceptable to the authorizing agency. Thus, system 10 is configured to receive entries, analyze those entries and present further queries in response if necessary until reaching an acceptable standard. Information may be requested via drop-down menus, checkboxes or other easily selectable options. System 10 may automatically provide entries based on data entered previously by the patient or administrative staff during the case intake or patient interview portions to the extent possible.

It should be readily apparent that system 10 may incorporate any other method for allowing the user to select the appropriate data for entry, including asking the user to select from a series of preprogrammed queries or statements to decide the appropriate entry.

System 10 may also input information into prose using data collected. For example, based on the scheduled appointment date and time stored in the case file and shown in screen 112, and data collected regarding the time the patient arrived at the facility, system 10 may generate a report with a statement such as "the patient, John, arrived very early for his scheduled appointment at 10 AM on Wednesday, Nov. 7, 2007." System 10 can be configured to select to input language such as "very early," "early,", "on time," "late," or "very late" in this sentence based on a preset relationship between the time arrived, the difference in time between the time arrived and the appointment time, and the language options. For example, recording that the patient arrived between 15 minutes to 1 hour prior to the scheduled appointment time might be operatively associated by system 10 to insert the language "early" in the above sentence, whereas over 1 hour might be operatively associated with the language "very early" by system 10. Also, the use of gender-specific pronouns, such as "his" or "her" may be automatically selected by system 10 based on the patient's gender.

Alternatively, a user may be presented with the statement "The patient arrived . . . " and then asked if "very early" is appropriate by checking or clicking on a "yes" button or a "no" button. By clicking on the "no" button, the user would then be asked if "early" is appropriate, and presented again with the option of clicking "yes" or "no." This would continue until the user reached "very late" and clicked "yes."

System 10 may use information entered in the case file and/or during the intake portion to select the language and form statements for the final report. If statements can not be completed, system 10 may also indicate that certain information should be asked and entered into system 10 during the appointment. Any information entered into system 10 may then be used to adjust the statement language, generate further questions and form statements for the report.

For example, assume the responses to the following questions shown above are as follows:

How did the patient arrive for the appointment? "Drove self"

Who did the patient arrive with for the appointment? "Wife"

Who did the patient arrive with for the appointment? "Friend"

The name entered in the field is "Paul"

Who did the patient arrive with for the appointment? "Nobody else"

System 10 may then access the patient case file or data collected from other questions to determine the wife's name and add the statement "John drove to the office for the appointment and came with his wife, Yoko and his friend, Paul" to the final report. In another example, the patient may be asked if he or she is suffering from pain during the appointment. If the patient indicates "no" the sentence "the patient is not experiencing noteworthy pain at this time" may be added to the report. If the patient indicates "yes" a query may be made of any sort, such as the ones shown above, which allows the user to enter information relating to the location of the pain on the patient's body, the frequency the pain occurs, how long the pain lasts, and any other pertinent information relating to the pain for inclusion in the case file. The information would be formatted into a sentence that reflects the information entered and incorporated in the report.

It should be readily apparent that the above examples are meant to illustrate the features of the embodiments of the present invention and clearly not meant to be limiting. The embodiments may include as many queries and selectable response options, as well as make any follow-up queries in response to the selected response options as necessary to obtain the information desired. In one embodiment, the queries are chosen so that the information obtained is capable of completing the case file and developing the report in the most efficient manner. System 10 may provide queries in an order that logically follows the arrangement of information contained in a report according to acceptable standards.

The provision of queries may be accomplished through the use of preprogrammed criteria or rules stored within a database and operatively associated with system 10. Queries are set forth to the user and patient during the case intake and patient interview portions. A data processor operatively associated with system 10 uses the criteria to analyze the response data in order to determine errors, inconsistencies, missing information or identify subject areas for further investigation. As a result of the analysis, further queries are presented through the user interface to be completed by the user during the appointment. These queries may be selected to obtain missing information, further clarify previously submitted information, follow-up on identified subjects, or other areas of importance, and may be included with the standard physician investigation and tests necessary to complete the report.

System 10 stores and formats data inputted in response to the queries into a suitable report. System 10 may also access data and use the preset criteria to format the report according to one or more agency requirements. A user of system 10 may actuate production of a report by selecting the patient and a particular agency authorized to receive and adjudicate such requests for assistance. The report or application will be prepared according to the applicable standards associated with the selected agency, and may also include any applicable specialized codes such as medical billing codes.

In one embodiment, the report is configured as sentences. Various sets or series of strings of words are preset for use by system 10 to eventually form sentences in the report. These word strings are intended to minimize the amount of data input necessary during the collection events. After data is collected during the intake and appointment data collection events, system 10 can use the data contained in the patient related case files to select or adjust portions of words contained in the preset strings of words, while also inserting some of the collected data into other portions of the preset strings of words to form completed sentences in the report. For example, the words strings may include portions which are changed for grammatical reasons depending on the data, and such changes may include the use of gender-specific pronouns or pluralizing. The collected data is associated with corresponding word strings and inserted therein to form complete sentences for inclusion in the report. For example, specialized test results may also be inserted in strings of words that describe or apply to the specific test.

System 10 may automatically produce the report upon completion of the appointment event in accordance with the standards associated with the agency entered in screen 104. System 10 may be further configured to automatically enter a physician's signature electronically, and may subsequently transmit the report or application electronically.

Thus, in one embodiment, system 10 is actuated by the physician during the appointment so that data obtained by the physician during the appointment can be directly entered into the format for submittal to the state agency and the report or application completed immediately upon completion of the appointment.

System 10 may also incorporate a final check system to confirm that no further data is necessary prior to the end of the appointment or that all statements are properly completed. For example, at the culmination of the patient's appointment, the physician or user may click on a final check button, if the check is not automatic, to conduct a second analysis in order to confirm that all the information necessary to complete a compliant report is present in the case file. If required elements are missing or statements are not properly completed, system 10 may notify the user or physician and identify the issue. The notification may be prior to the patient leaving the point of service. The notification may involve the presentation of the report to the user in a final form which also allows for editing of the report. The user may be presented with each problematic statement through a user interface. These portions may also be highlighted or otherwise marked for the user's convenience. The user may be provided with options to address the issues, such as generating the report with the identified portion unedited, removing the identified portion sentence or editing the portion prior to generating the examination report.

For example, in Nevada, the government agency with authorization to deny or grant disability benefits is the Bureau of Disability Adjudication of the Nevada Department of Human Resources. In this example, system 10 accesses preset criteria which will be used to compare the data provided by the patient interview to determine if further queries should be presented to the patient by the physician during the appointment in order to obtain all the information necessary to provide a compliant CE report, and then arrange the total information in the case file in the appropriate format for submittal as a CE report to the Bureau.

Two examples of CE reports (acceptable to the Nevada Department of Human Resources) generated by one embodiment of the invention such as system 10 are shown below.

EXAMPLE 1

DEPARTMENT OF HUMAN RESOURCES PHYSICIAN'S R.T.D.S. REPORT

BUREAU OF DISABILITY ADJUDICATION
CLAIMANT: DOE, WILLIAM SSN: 100-00-0000
PHYSICIAN: L. D. Larson, Ph.D. DATE SEEN: Jul. 12, 2007
UNIT:
ADJUDICATOR: J. MOORE
ARRIVAL INFORMATION: The patient arrived very early (45 minutes) for his scheduled appointment at 3:00 p.m. on Thursday, Jul. 12, 2007. William arrived for the appointment by bus. The patient does not have a Nevada driver's license. The patient reported that when he was driving regularly in the past, he never caused any accidents. About 30 years ago, he was charged with a DUI, but he thought it was reduced to a conviction of reckless driving. William said he stopped driving and elected to ride the bus about seven years ago, mainly for economic reasons. The patient reported that the trip to the office took about two hours. This is a fairly reasonable estimate of travel from Las Vegas Boulevard and Charleston, by city bus. The patient elected to complete the paper-and-pencil intake forms. The patient's writing was very neat and highly legible. William stated that his addressed had recently changed. His new address is: 15 S. Rainbow Boulevard, Las Vegas, Nev. 89000.

William is a 57 year-old Caucasian male. He was 5 feet, 8 inches tall and weighed 150 pounds. His weight has reportedly changed appreciably over the past year. William indicated that he may have gained a few pounds. He reported that his stomach was feeling a "little distended." William stated that he must walk slowly and not very far. He easily runs out of breath and his legs will begin to hurt. The patient was adequately dressed in casual clothing appropriate for the season. William was sufficiently well groomed. The patient stated that he will occasionally get cramps in his feet, legs and hands.

HISTORY OF ILLNESS: Included with the BDA file for this patient was the following background document:

(1) Medical Records: Completed by University Medical Center, Las Vegas, Nev., Mar. 18, 2006 to Mar. 21, 2006. The patient was admitted to the hospital with abdominal pains and distention. He was found to have massive ascites. He had a history of coronary artery disease, congestive heart failure, and myocardial infarction in February 2002. He had a known tobacco use of one and a half packs per day and heavy ethanol abuse. During his hospital stay, the patient benefited from a work work-up for liver cirrhosis, as well as diagnostic paracentesis. Diagnoses for this patient included liver cirrhosis, ascites, portal hypertension, coronary artery disease, and ethanol abuse. Discharge diagnoses included Plavix and Norvasc.

When asked to describe his current problem or condition, William stated, "Back pains, leg pains, difficulty in being on my feet, shortness of breath. I get occasional cramps." William said that he started having significant problems about a year ago. He was getting medical attention at UMC. He got really distended in the beginning of 2006 and he was hospitalized. Fluids were pumped from his stomach area and he was diagnosed with cirrhosis. He also was diagnosed with heart disease and pancreatitis. William indicated that he started drinking in 1965. He mainly drank beer, but he also liked vodka. William said that he stopped drinking after he was diagnosed with cirrhosis. The patient has been smoking since he was about 14 years. He would usually smoke about two or three packs a day. William said that he has tried to cut back to about half a pack per day.

The patient provided the following medical history:
YEAR HEALTH PROBLEM TREATMENT RECEIVED

| | | |
|---|---|---|
| 2007 | Pancreatitis | Medications |
| 2006 | Cirrhosis | Medications |
| 2002 | Heart attack | Medications |

The patient provided the following information about current prescription medications:

Folic acid prescribed by Dr. Mulamalla for vitamin deficiency

Furosemide prescribed by Dr. Dhansu for heart problems

Lexapro prescribed by Dr. Bist for depression

Mirtazapine prescribed by Dr. Freedman for depression

Plavix prescribed by Dr. Calegari for heart problems

Potassium prescribed by Dr. Calegari for heart problems

Simvastatin prescribed by Dr. Mulamalla for cirrhosis

Spironolactone prescribed by Dr. Calegari for heart problems

William has had discomforting pain in his back for six months to one year. The pain occurs daily so the patient takes medicine occasionally plus reduces pain by lying down. The patient does not have seizures.

Substances reportedly used by the patient in the past included caffeine, tobacco, alcohol, and marijuana. Substances still being used reportedly included caffeine and tobacco. William has not been in any alcohol treatment program in the past year. William has not participated in alcohol self-help groups in the past. He has not been in a drug rehab program this past year.

PERSONAL AND FAMILY HISTORY: William was born on Aug. 27, 1949 in Vineland, N.J. His birth father is unknown. His birth mother is unknown.

His family included two brothers and two sisters. William was the fifth child in the family. The family moved frequently while he was growing up. The patient left high school his senior year but later obtained a GED. William attended all regular classes in school. He described himself as an above average student. The patient was active in the following extra curricular activities while attending school: Football, baseball, Glee Club, and drama.

He identified his primary occupation as public relations for more than ten years. The patient last worked at the Las Vegas Club as a race and sports book writer last year. He had worked at this job for about four years. New owners took over the casino and the sports book was shut down. When asked about plans to work in the future, William indicated "No, I was told that I was disabled by the doctor. When I would go looking for work, I would get out of breath. If I tried to put in eight hours of work, I don't think I could make it."

The patient reported that he could not work at all. The patient is not applying for work. He does not plan to return to work.

William provided the following information about prior work experience:

START END WORK DESCRIPTION 2002 2006 Race and sports book writer 1995 2001 Proof reader and verifier 1985 1995 Heating and air conditioning installer and sheet metal worker 1975 1985 Outside sales for Yellow Pages 1965 1975 Various jobs (store clerk, driver, and stocker)

The patient has lived more than ten years in Southern Nevada. He lives in a rented apartment. Current sources of support for the patient include food stamps and Clark County Social Services for rent and medical assistance.

The patient provided the following marital or relationship history:

YEAR MARITAL CHANGE DETAILS

1975 Married Married

1985 Divorce Divorced

Patient indicated he is not in trouble with the law now.

MENTAL STATUS EXAMINATION: Mood was pleasant and stable. Affect was normal and consistent with the content of the conversation. In describing himself, William said, "I am intelligent, friendly, able to talk with anybody. I will voluntarily try to help people, until I find that they are trying to bite me. I try to be neat, clean, and orderly." Facial expressions and motor activity for this patient were not excessive.

Interaction style was open. Speech quality was normal in rate and volume. Speech pronunciation was clear. Concerning organization of language, the patient showed no problem in expressing himself. The patient was reporting no auditory or visual hallucinations at this time. During the assessment, William did not appear to be responding to any internal stimuli. A history of suicide or harm to others was indicated by the patient. The patient stated that he did attempt suicide about a year ago when he found out that his cirrhosis was irreversible. He cut his wrists. He later thought better of the situation and put bandages on his arms. William went to SNAMHS for assistance. He has now been getting support from Clark County Social Services. He has been prescribed medications for depression, which may be helping somewhat. No prior history of mental health treatment was reported. Current suicidal or homicidal ideation was denied.

In examining cognitive functions, William attained the following results:

The patient was oriented to person, place, time, and purpose of visit to office.

Digit Span:

(Digits Forward) 9/16, 0 errors at 2, 3, 4 & 6 digits 1 error at 5 digits 2 errors at 7 digits (Digits Backward) 6/14

0 errors through 4 digits 2 errors at 5 digits

Scaled Score: 9 (Average)

Serial 7's—The patient made the following calculations: 93, 86, 79, 72, 65, confused, 48(error), 41, 34, 27, 20, 13, 6.

Serial 3's—The patient stated: 17, 14, 11, 8, 5, 2.

Short-term memory was judged to be excellent. The patient was able to remember the examiner's name. In recall of other items that were presented, he could freely recall all five items. Delayed memory was excellent. The patient again recalled the examiner's name. In recall of other items that were presented, he could freely recall all five items. Immediate memory was judged to be within average limits based on digit span trials. Fund of general information was good. Awareness of current events was good.

A sampling of the patient's vocabulary indicated that William understood the meaning of simple words such as "recover" and words of slightly greater complexity such as "contemplate." He also demonstrated knowledge of more complex words such as "averse" and "perjury." Abstraction ability was found to be adequate based on the patient's awareness of various similarities and proverbs. For instance, when William was asked to compare the way in which birth and death are alike, he was able to express that both relate to the cycle of life. Responses to proverbs tended to reflect traditional interpretations. Good judgment was demonstrated on a variety of comprehension probes. As an example, when asked, "What would you do if you had a leaky faucet?" William was able to provide a commonsense solution for fixing the leak. He was also able to explain how credit cards might cause problems for people.

When asked to draw various geometric shapes, William was able to make appropriate discriminations between simple shapes, such as, a circle, square, triangle, and cross. Discriminations between simple figure sizes (dime compared to a quarter, larger versus smaller) were not difficult for this patient. He had no difficulty in drawing slightly more complex and abstract shapes, such as, a stop sign or the state of Nevada. William was able to show a reasonable spatial relationship between geographic points, such as, the relative location of a city within a state. The patient did correctly draw the face of a clock with hour and minute hands positioned at 20 minutes to 10:00 o'clock as directed. William demonstrated adequate ability in completing a multiple-step task involving drawing appropriate parallel lines across the page. Line quality for this patient was adequate, with steady movement and even pressure. William was able to correctly spell each of the words requested by the examiner.

Daily Activities:

William reported that he gets up each morning at 9:00 AM. The patient stated that his morning is spent doing the following activities: fixing breakfast, showering, getting dressed, and watching TV. At lunchtime William said "I make my own lunch and read the paper." Afternoon activities include: solving crossword puzzles and preparing his own dinner. William's usual evening activities include: watching TV. The patient goes to bed at 10:00 PM. William described the quality of his sleep in the following manner: "Easily awakened."

The patient provided the following information regarding specific activities he can or cannot perform. When the patient goes out he rides the bus. William can go shopping alone. William can make his own shopping list. The patient can pay the right amount and count change. He doesn't have a checkbook and cannot write checks. He can bathe himself in a tub or shower. He can dress himself and take care of his hair. He can take care of his clothing.

The patient claimed that he can concentrate on a task until it is finished. He reported that he can understand and remember what he reads and sees on TV. Things that are reported to be of interest to the patient include: keeping up with the news.

Functional Assessment—Adult:

A. ASSESSMENT OF ABILITY TO UNDERSTAND, REMEMBER, AND CARRY OUT AN EXTENSIVE VARIETY OF COMPLEX INSTRUCTIONS.

Based upon the above assessment interview and mental status examination results, this patient was judged to be functioning in the Average Range of intellectual ability. William would appear to have sufficient general cognitive ability to carry out tasks at this level of complexity. He is primarily reporting physical health problems that he feels are disabling.

B. ASSESSMENT OF ABILITY TO UNDERSTAND, REMEMBER, AND CARRY OUT DETAILED BUT UNCOMPLICATED INSTRUCTIONS.

See Section A above.

C. ASSESSMENT OF ABILITY TO UNDERSTAND, REMEMBER, AND CARRY OUT SIMPLE ONE OR TWO-STEP INSTRUCTIONS.

See Section A above.

D. APPROPRIATE INTERACTION WITH SUPERVISORS, CO-WORKERS, AND THE PUBLIC.

The patient was very pleasant and cooperative during today's evaluation. William appeared to have adequate social skills.

E. ASSESSMENT OF ABILITY TO MAINTAIN CONCENTRATION AND ATTENTION SUFFICIENT TO CARRY OUT SIMPLE ONE OR TWO-STEP TASKS.

William is capable of doing this.

DIAGNOSIS: AXIS I:

307.89 Pain Disorder Associated With Both Psychological Factors and a General Medical Condition 293.83 Mood Disorder Due to a General Medical Condition With Major Depressive Symptoms 303.90 Alcohol Dependence In Recent Remission Per Patient Report AXIS II: V71.09 No Diagnosis on Axis II AXIS III: See Background Medical Records AXIS IV: Psychosocial Stressors: 3—Moderate AXIS V: Current GAF: 50-55

Highest GAF Past Year: 50-55

PROGNOSIS: The prognosis for this patient is largely dependent upon his physical condition. William reported major health complications following a long history of alcoholism and tobacco use. He has recently become depressed secondary to his chronic health problems. The patient reported that he was scheduled for a BDA physical examination on July 18 or 19th. The results from this physical examination should be thoroughly reviewed to further formulate the prognosis for this patient.

MONEY COMPETENCE: William has sufficient general cognitive ability to manage his own personal finances. As long as he refrains from drinking, he should be capable of managing his on monetary benefits.

L. D. Larson, Ph.D.

Clinical Psychologist, NV

EXAMPLE 2

DEPARTMENT OF HUMAN RESOURCES PHYSICIAN'S R.T.D.S.

REPORT BUREAU OF DISABILITY ADJUDICATION

CLAIMANT: SMITH, POLLY SSN: 100-99-0000

PHYSICIAN: L. D. Larson, Ph.D. DATE SEEN: Sep. 11, 2007

UNIT:

ADJUDICATOR: J. MOORE

ARRIVAL INFORMATION: The patient arrived on time for her scheduled appointment at 4:00 p.m. on Tuesday, Sep. 11, 2007. Polly arrived for the appointment by bus. The patient stated that her mother "did everything" on the computerized intake process. Polly said that she does know how to use a computer, but she does not know how to type very fast.

Polly is a 16 year-old African-American female. She was 5 feet, 11 inches tall and weighed 183 pounds. Her weight has reportedly remained stable with respect to growth over the past year. No problems were observed in the patient's ambulation, balance, or posture. The patient was adequately dressed in casual clothing appropriate for the season. Polly was sufficiently well groomed. Involuntary movements or tremors were not observed in this patient.

HISTORY OF ILLNESS: No past medical records or background documents were included with the BDA file for this patient.

When asked to describe her current problem or condition, Polly's mother stated, "I don't want her to get hurt. She needs to learn to calm down or she might get hurt." According to the patient, she does have difficulty in her social relationships. Polly said "I don't have any friends. Kids don't get along with me."

Polly is not experiencing noteworthy pain at this time. The patient does not have seizures.

PERSONAL AND FAMILY HISTORY: Polly was born on Nov. 8, 1990 in Detroit, Mich. Her birth father was Joseph Jones, a person with unknown occupation. Her birth mother was Anna Smith, a contract employee. Her birth family included three brothers. Polly was the second child in the family. The family moved frequently while she was growing up. Polly is in the tenth grade and attends all regular classes.

Home behavior problems were commented on by the patient and her mother. At home, Polly's behavior has apparently shown some improvement. Anna described Polly as "running hot and cold, up and down, and usually mad at the world." Polly said that she talks too much at home and she does irritate everybody. She said that her mother has to tell her "about 40 or 50 times" to do something.

School behavior problems were commented on by Polly and her mother. The patient's mother, Anna, said "Polly is in behavioral school right now. She had been kicked out of the Detroit schools when we used to live there. When we first moved to Las Vegas, we tried to keep her in regular classes, but she only lasted less than a week." Anna added that Polly has a very bad temper and "when she blows, she is gone." Polly herself said "I have behavioral problems at school, and that's why I am at opportunity school. I was fighting, hitting, name calling, cussing out the teachers, talking back to the principal, and bringing contraband into the school."

The following information was obtained from a Developmental History Questionnaire: Currently, the patient is living with her natural single parent in a rented apartment. There are no standing custody disputes regarding Polly. Polly's mother, Anna Smith reported that the pregnancy with Polly was unplanned and was her mother's fifth pregnancy. Anna was 22 years old and Joseph was 32 at the time of the pregnancy. They were not married at time of pregnancy. Polly's mother did not use hard drugs during the pregnancy with Polly. Anna smoked less than one pack a day and did not drink alcohol during the pregnancy. There were no known complications with this pregnancy. Polly's mother did not have illness or medical complications and she had bleeding during the pregnancy. Labor was normal and delivery was head first. The baby was born full-term.

Polly weighed seven pounds at birth. She did eat well and sleep well during the first few months of life. She did not have breathing problems the first few months of life. Her mother described her as an active, persistent, and happy baby Polly reached the normal developmental milestones on time and walked alone at 12-15 months old. She was toilet trained between 1½ and 3 years old. Toilet training was not a battle. She was not having elimination problems. She started talking on time. Polly has had a head injury but never had broken bones or accidental poisoning. No hearing or vision problems were indicated. Her mother knows of no abuse toward Polly.

Polly's parents reportedly had no significant problem in their relationship.

Polly attended day care prior to three years of age. She went to nursery school and kindergarten. She did not have trouble learning to read. In her reaction to entering elementary school Polly was happy and had problems with teachers. Polly reportedly does have behavior problems in school now. Anna indicated that the patient did not have learning problems in school now. Special testing has been conducted. Polly has never been placed in special classes in the past. She is not now in special classes.

Her mother reported that she has lived in the Southern Nevada area for two years. Polly's mother said that Polly's sources of support include child support and $222.00 per month. The patient's family history was positive for emotional problems, delinquency, alcoholism, and drug abuse.

MENTAL STATUS EXAMINATION: Mood was pleasant and stable. Affect was normal and consistent with the content of the conversation. Interaction was open. Speech quality was normal in rate and volume. Speech pronunciation was clear. Concerning organization of language, the patient showed no problem in expressing herself.

According to her mother, Polly does not appear to be responding to any internal stimuli (auditory or visual hallucinations), but often seems to be in a world of her own. She has in the past wished to die or to hurt herself. Polly has never tried to harm herself.

She has not tried to hurt pets or other children. The patient's mother is aware or suspects that Polly has experimented with tobacco, marijuana, and alcohol. A significant problem with substance abuse is not suspected. Polly has not received outpatient counseling for substance abuse. Inpatient drug rehabilitation has not been received.

The patient was oriented to person, place, and time, but not purpose of visit to office.

Digit Span:
(Digits Forward) 0/16,
No results with 0 errors.
2 errors at 2 digits
(Digits Backward) 0/14
0 errors through 0 digits
2 errors at 2 digits
Scaled Score: 1 (Extremely Poor)

Recall of age-appropriate factual information and general comprehension would suggest that long-term memory is inadequate or poorly developed. Simple addition and subtraction problems were not accurately solved. A sample of the patient's vocabulary indicated that Polly exhibited difficulty in understanding the meaning of even simple words such as "clock" and "umbrella".

Abstraction ability was found to be poor based on the patient's lack of awareness of various age-appropriate similarities. Poor judgment was demonstrated on a variety of comprehension probes. As an example, when asked, "What should you do if a girl much smaller than you starts to fight with you?" Polly was not able to indicate that she should walk away or go tell an older person.

DAILY ACTIVITIES: Information regarding the patient's daily activities was obtained from Polly and her mother. Polly gets up each morning at 6:30 AM. Her morning is spent doing the following activities: getting ready for school and going to school. At lunchtime Polly's mother said "Polly usually talks with other children at school." Afternoon activities include: getting out of school, going home, maybe going swimming if hot out or watching television. Polly's usual evening activities include: watching television, taking a shower and getting ready for bed. The patient goes to bed at various times between 10:00 and 11:30 PM. Polly's mother described the quality of her sleep in the following manner: "Sleeps hard and sound."

The patient and her mother provided the following information regarding specific activities that Polly can or cannot perform. Polly's social activities include often writing to or receiving mail from family and friends. Recreational activities include shopping, walking, swimming, visiting at friend's home, going to movies, and listening to music. Polly can do the following chores around the house: cooking and laundry. She can bathe herself in a tub or shower. She can dress herself and take care of her hair. She can take care of her clothing. The patient cannot concentrate on a task until it is finished. She can understand and remember what she sees on TV but not what she reads. Things reported to be of interest include: conversation. Hobbies include braiding hair. Crafts indicated by the patient include drawing & writing.

PSYCHOMETRIC TEST RESULTS: WECHSLER ADULT INTELLIGENCE SCALE—THIRD EDITION—
On this administration of the WAIS-III, Polly obtained the following scores:

Verbal Scale I.Q. score: 86
Performance Scale I.Q. score:94
FULL SCALE I.Q. SCORE: 89

The following sub-test scale scores were obtained: VERBAL TESTS

Information 8
Digit Span 9
Vocabulary 5
Arithmetic 7
Comprehension 10
Similarities 7
PERFORMANCE TESTS
Picture Completion 5
Picture Arrangement 9
Block Design 13
Matrix Reasoning 9
Digital Symbol 10

The patient was very cooperative and pleasant throughout today's administration of the WAIS-Ill. No unusual test-taking behaviors were exhibited that would have detracted from the patient's overall test performance. During the Block Design sub-test, Polly recalled taking a similar type of test when she was in school. Sub-test scores for this patient were somewhat varied, with the patient showing weaker scores on tasks associated with word knowledge and attentiveness to detail. She did extremely well on Block Design, which involves physical problem-solving and matching-to-sample abilities. The patient's general comprehension and speed of manual operations were also relatively strong. Based upon the patient's Full Scale I.Q. score of 89, Polly was found to be functioning in the upper end of the Low Average range of intellectual ability.

Functional Assessment—Children:

A. ASSESSMENT OF ABILITY TO UNDERSTAND, REMEMBER, AND CARRY OUT AN EXTENSIVE VARIETY OF COMPLEX INSTRUCTIONS AS APPROPRIATE FOR AGE AND CONTEXT.

Based upon the above assessment interview and psychological test results, this patient was found to be functioning in the upper end of the Low Average range of intellectual ability. Polly would appear to have sufficient general cognitive ability to carry out most types of tasks at this level of complexity.

B. ASSESSMENT OF ABILITY TO UNDERSTAND, REMEMBER, AND CARRY OUT DETAILED BUT UNCOMPLICATED INSTRUCTIONS AS APPROPRIATE FOR AGE AND CONTEXT.

See Section A above.

C. ASSESSMENT OF ABILITY TO UNDERSTAND, REMEMBER, AND CARRY OUT SIMPLE ONE OR TWO-STEP INSTRUCTIONS AS APPROPRIATE FOR AGE AND CONTEXT.

See Section A above.

D. APPROPRIATE INTERACTION WITH TEACHERS AND PEERS.

This has been an area of significant concern for the patient. She has failed to behave appropriately in the regular classroom setting and now attends a specialized behavioral school program. Polly reportedly has been aggressive towards peers and teachers and has been involved with fights and other forms of misconduct. Apparently, her behavior has not resulted in any arrests or contact with juvenile authorities.

E. ASSESSMENT OF ABILITY TO MAINTAIN CONCENTRATION AND ATTENTION SUFFICIENT TO CARRY OUT SIMPLE ONE OR TWO-STEP TASKS.

The patient is judged to be capable of doing this.

DIAGNOSTIC IMPRESSIONS:

AXIS I: 313.81 0 ppositional Defiant Disorder Moderate
312.8 Conduct Disorder (Provisional)
AXIS II: 799.9 Diagnosis Deferred on Axis II
AXIS III: Non-contributory
AXIS IV: Psychosocial Stressors: 3—Moderate
AXIS V: Current GAF: 55-60
Highest GAF Past Year: 55-60
PROGNOSIS: The prognosis for this patient is mixed. Maturation is likely to benefit this patient. The family would benefit from therapy to help instill better boundaries and communication styles for Polly. The fact that Polly has not required juvenile authority contact is suggestive of a more salutary prognosis.

L. D. Larson, Ph.D.
Clinical Psychologist, NV

In general, the present disclosure is directed to systems and methods for facilitating the efficient collection of data and arranging the data in accordance with requirements set forth by agencies that administer benefits and assistance based on need. The present invention may also be used to generate general statistical information based on the parameters contained in each of the patient data files stored in memory. For example, statistics relating to the numbers of patients with common personal histories, ailments or specialized test scores may be generated for informational or comparative purposes, or analysis of trends over time.

Although exemplary and preferred aspects and embodiments of the present disclosure have been described with a full set of features, it is to be understood that the disclosed system and method may be practiced successfully without the incorporation of each of those features. It is to be further understood that modifications and variations may be utilized without departure from the spirit and scope of this inventive system and method, as those skilled in the art will readily understand. Such modifications and variations are considered to be within the purview and scope of the appended claims and their equivalents.

What is claimed is:

1. A computer-implemented method of generating a patient examination report related to Social Security disability benefits during an appointment, comprising the steps of:
 a) storing in computer memory a first set of data relating to a patient and Social Security Administration as an electronic patient data file;
 b) presenting on a display a first query set relating to a patient at a first event;
 c) storing in said computer memory a first response data received in response to the first query set in the electronic patient data file;
 d) analyzing by means of a computer processor instructed by a computer program the electronic patient data file according to a preset criteria to identify further patient related data to be collected, wherein the electronic patient data file must satisfy the preset criteria in order to automatically generate a patient examination report complying with U.S. Social Security Administration laws and regulations;
 e) selecting by means of said computer processor instructed by a computer program further queries to collect further patient related data based on the analysis;

f) presenting on said display a second query set at a second event, wherein the second query set includes the selected further queries;

g) storing in said computer memory a second response data received in response to the second query set in the electronic patient data file; and h) generating by means of said computer processor instructed by a computer program the patient examination report in accordance with the accepted standards of the U.S. Social Security Administration laws and regulations whereby generating said report includes combining word strings stored in said computer memory with received data to form completed sentences in said patient examination report, said examination report capable of being completed at the second event.

2. The method according to claim 1, further comprising utilizing the first query set to collect information relating to the medical background and social history of the patient.

3. The method according to claim 1, wherein the first event and second event occur during the appointment.

4. The method according to claim 1, further comprising utilizing the preset criteria to identify possible errors, data inconsistencies, and missing information in the patient data file.

5. The method according to claim 1, further comprising utilizing the preset criteria to identify subject areas for further investigation based on the accepted standards of the Social Security Administration.

6. The method according to claim 1, further comprising selecting the further queries to clarify possible errors, data inconsistencies, and missing information in the patient data file based on the accepted standards of the Social Security Administration.

7. The method according to claim 1, wherein the second query set includes queries relating to the health of the patient.

8. The method according to claim 1, wherein the second response data includes the results of specialized tests conducted during the second event.

9. The method according to claim 1, wherein the step of generating the patient examination report related the Social Security disability benefits, further comprises the steps of:

adjusting by means of said computer program a first portion of a preset strings of words to form a grammatically correct sentence in the examination report based on the data contained in the patient data file; and inserting by means of said computer program data contained in the patient data file into a second portion of the preset string of words to form a complete sentence in the examination report.

10. The method according to claim 1, further comprising the steps of:

analyzing by means of said computer program the patient data file according to the preset criteria after storing the second response data;

identifying by means of said computer program any insufficient patient related data;

presenting by means of said computer program the identified insufficient patient related data in an interface; and receiving by means of said computer program an instruction to generate the examination report with the insufficient data, allow the insufficient data to be edited, or remove the insufficient data from the examination report.

11. The method according to claim 10, wherein the step of analyzing the patient data file according to the preset criteria after storing the second response data includes the steps of:

inserting by means of said computer program the patient related data contained in the patient data file into a series of preset strings of words to form sentences in the examination report;

analyzing by means of said computer program the examination report to identify sentences therein containing insufficient patient related data; and presenting by means of said computer program each of the identified sentences via said display, wherein the display is configured to receive an instruction to generate the examination report with the identified sentence, allow the identified sentence to be edited, or remove the identified sentence from the examination report.

12. A system for generating a patient examination report related to Social Security disability benefits during an appointment, comprising:

a) a computer database for storing a first set of data relating to a patient and the Social Security Administration as an electronic patient data file;

b) an electronic interface for presenting a first query set relating to a patient at a first event;

c) a computer database for storing a first response data received in response to the first query set in the electronic patient data file;

d) a computer processor programmed for:
  i) analyzing by means of an instructional computer program the electronic patient data file according to a preset criteria to identify further patient related data to be collected, wherein the patient data file must satisfy the preset criteria in order to generate a patient examination report complying with U.S. Social Security Administration laws and regulations;
  ii) selecting by means of said instructional computer program further queries to collect further patient related data based on the analysis;

e) an electronic interface for presenting a second query set at a second event, wherein the second query set includes the selected further queries; and f) a computer database for storing a second response data received in response to the second query set in the electronic patient data file;

wherein the computer processor generates the patient examination report in accordance with the U.S. Social Security Administration laws and regulations prior to the end of the second event whereby generating said report includes combining word strings stored in memory with received data to form completed sentences in said patient examination report.

* * * * *